United States Patent [19]

Gauglitz et al.

[11] Patent Number: 5,262,842
[45] Date of Patent: Nov. 16, 1993

[54] OPTICAL SENSOR HAVING A WAVE GUIDE SUBSTRATE WITH INTERFEROMETER INTEGRATED THEREIN

[75] Inventors: Günter Gauglitz, Tübingen-Hagelloch; Jan Ingenhoff, Tübingen; Norbert Fabricius, Hockenheim, all of Fed. Rep. of Germany

[73] Assignee: IOT Entwicklungsgesellschaft für integrierte Optiktechnologie mbH, Waghäusel-Kirrlach, Fed. Rep. of Germany

[21] Appl. No.: 780,867

[22] Filed: Oct. 18, 1991

[30] Foreign Application Priority Data

Oct. 19, 1990 [DE] Fed. Rep. of Germany ....... 4033357

[51] Int. Cl.$^5$ ................................................ G01B 9/02
[52] U.S. Cl. ..................................... 356/345; 356/361; 385/12
[58] Field of Search ................. 356/345, 361; 385/128, 385/122, 12, 13, 132; 250/227.27, 227.19

[56] References Cited

U.S. PATENT DOCUMENTS

| | | | |
|---|---|---|---|
| 4,712,865 | 12/1987 | Hsu et al. | |
| 4,842,783 | 6/1989 | Blaylock | |
| 4,936,645 | 6/1990 | Yoon et al. | 385/132 |
| 4,940,328 | 7/1990 | Hartman | 356/345 |
| 4,969,711 | 11/1990 | Rogler et al. | 385/128 |
| 5,004,914 | 4/1991 | Vali et al. | 250/227.27 |
| 5,073,024 | 12/1991 | Valette et al. | 356/345 |

FOREIGN PATENT DOCUMENTS

| | | |
|---|---|---|
| 0230520 | 8/1987 | European Pat. Off. |
| 0487992 | 6/1992 | European Pat. Off. |
| 3723159 | 1/1988 | Fed. Rep. of Germany |
| 3832185 | 3/1990 | Fed. Rep. of Germany |
| WO90/05322 | 5/1990 | Int'l Pat. Institute |
| 2228082 | 8/1990 | United Kingdom |

OTHER PUBLICATIONS

"Integrated optical components in substrate glasses" by Ludwig Ross, Glastech. Ber. 62 (1989) Nr. 8, pp. 285 to 297.

Primary Examiner—Samuel A. Turner
Attorney, Agent, or Firm—Walter Ottesen

[57] ABSTRACT

A sensor for detecting substances including hydrocarbons includes an integrated optical interferometer in the form of a Mach-Zehnder interferometer having a measuring arm and a comparison arm in a wave guide substrate. A polymer such as polysiloxane is applied as a superstrate to the wave guide in the region of the measuring arm. This superstrate can be penetrated by the substance to be detected. Swelling response, gas absorption, refractive index of the polymer and doping with chromophores or fluorophores, layer thickness and layer length are all parameters which can be adapted for a substance-selective performance. Other means of selection include various superstrates on a number of interferometers mounted parallel on a chip and polychrome measurements in combination with methods of pattern recognition constitute further means of selection.

14 Claims, 6 Drawing Sheets n-Pentane n-Hexane n-Heptane n-Octane n-Pentane n-Hexane n-Heptane n-Octane

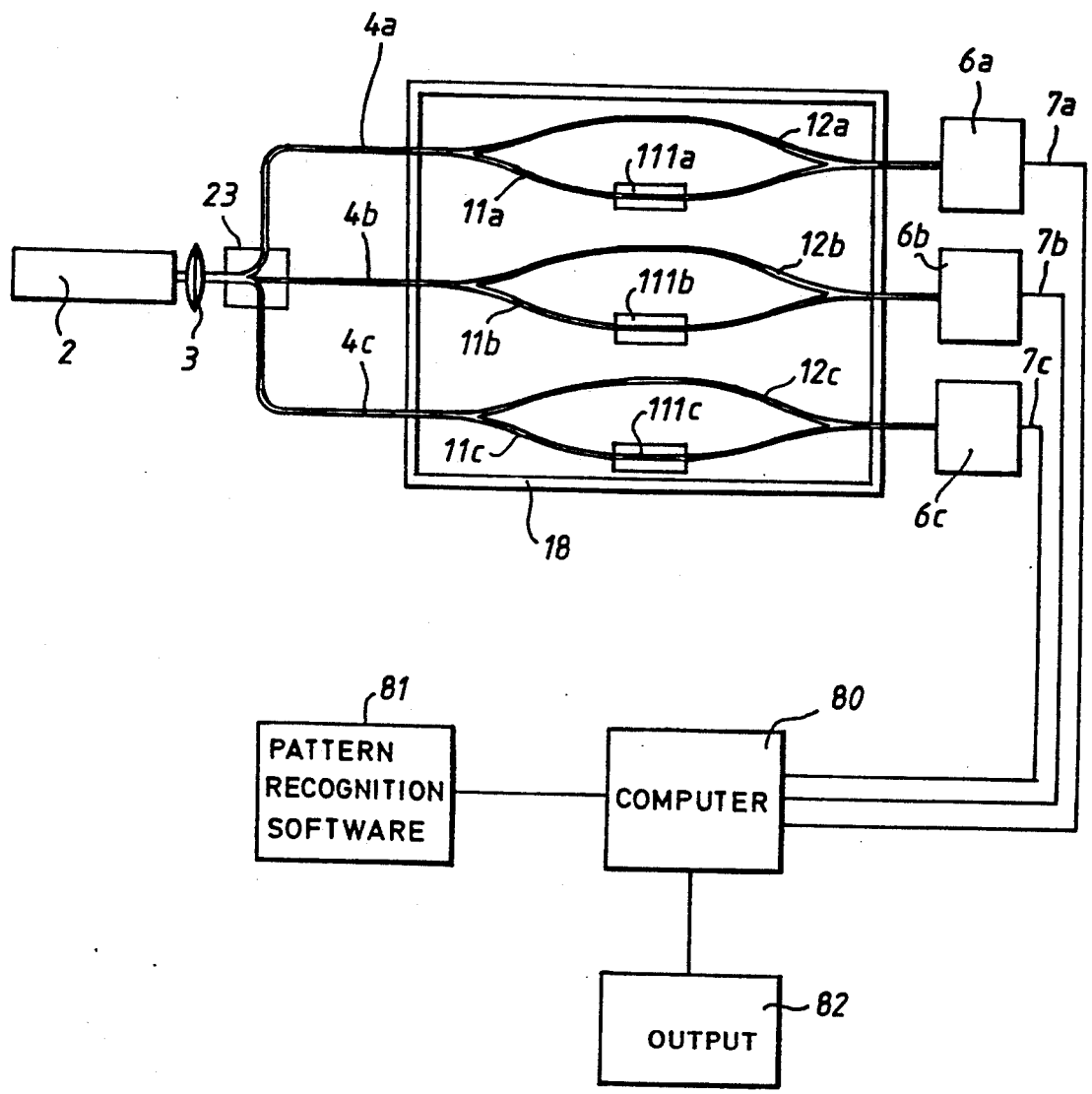

OPTICAL SENSOR HAVING A WAVE GUIDE SUBSTRATE WITH INTERFEROMETER INTEGRATED THEREIN

FIELD OF THE INVENTION

The invention relates to a sensor for detecting a substance with optical means.

BACKGROUND OF THE INVENTION

German published patent application DE 3,832,185 A1 discloses a moisture sensor which utilizes the moisture-dependent refractive index change of a boundary layer in an interferometer. The moisture-sensitive layer is arranged between porous reflectors.

U.S. Pat. No. 4,712,865 discloses the utilization of polysiloxanes in fiber-optic gas sensors; however, information as to the configuration of a sensor is not provided.

Integrated optical Mach-Zehnder interferometers are disclosed in the paper by Ludwig Ross entitled "Integrated Optical Components in Substrate Glasses", published in "Glastechnische Berichte" Volume 62 (1989), Number 8, pages 285 to 297.

The use of Mach-Zehnder interferometers is disclosed in the article of J. Dakin et al entitled "Optical Fiber Sensors; Principles and Components", published by Artech House, Boston, London 1987 without a superstrate layer defining a hydrogen sensor.

SUMMARY OF THE INVENTION

It is an object of the invention to provide a sensor for detecting a substance which can be produced utilizing integrated optics and is produced to be compact, robust and at low cost in many variations, adapted to specific measuring tasks. It is also an object of the invention to provide such a sensor having a short response time and a low hysteresis.

The sensor of the invention for detecting a substance includes an integrated optical interferometer having a measurement arm and a comparison arm in a wave guide substrate. A polymer is applied as a superstrate to the wave guide in the region of the measuring arm with this superstrate being penetrable by the substance to be detected. The parameters which can be varied for the specific adjustment of the substance to be detected include: light wavelength, functional groups of polymers and degrees of polymerization and the inclusion of chromophores or fluorophores.

The layer thickness of the polymer and the length of the superstrate on the measuring arm are also essential parameters.

The substance to be detected then effects a change of the light propagation in the measuring arm by means of two mechanisms. First, by changing the refractive index of the superstrate and, secondly, by changing the layer thickness by swelling. The last-mentioned mechanism is especially applicable to very thin polymer layers which are penetrated by the light wave at total reflection even up to the ambient air.

BRIEF DESCRIPTION OF THE DRAWINGS

The invention will now be described with reference to the drawings wherein.

DESCRIPTION OF THE PREFERRED EMBODIMENTS OF THE INVENTION

Figure 1:
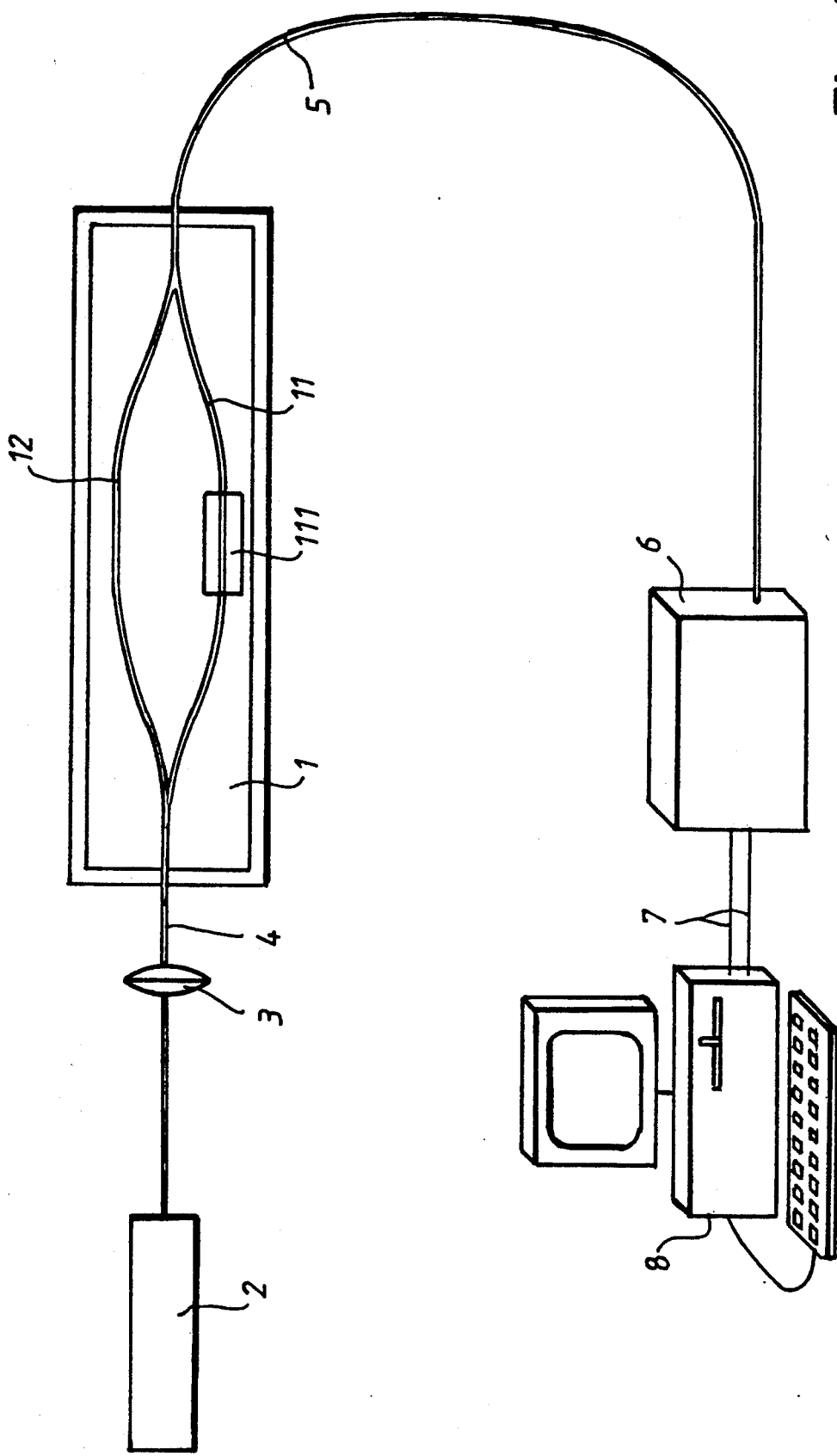
FIG. 1 is a schematic of an embodiment of the sensor of the invention including an illumination device, detecting device and evaluating device.

FIG. 1 shows an integrated optical Mach-Zehnder interferometer 1 realized on a glass substrate. The interferometer 1 includes a measuring arm 11 and a comparison arm 12. A polymer layer is applied as a superstrate 111 to the measuring arm 11. This polymer layer can be charged in any desired manner with gases, vapors or liquids where it is intended to detect their substance content.

The light source 2 can be a laser or a spectral lamp. The interferometer 1 is illuminated via the light source 2, an objective 3 and, as may be required, a light-conducting fiber 4.

The interfered light is conducted via a second light conductor 5 from the output of the interferometer 1 to the detector 6. A signal line 7 connects the detector 6 to the evaluating device 8 which can be a normal personal computer with suitable software. The evaluating device 8 indicates measurement curves and possibly provides a pattern comparison with known measurement curves.

The Mach-Zehnder interferometer 1 is produced by means of an ion exchange in a glass substrate while using photolithographic processes. The wave guides of the two interferometer arms 11 and 12 have a spacing of approximately 1 mm, 5 $\mu$m diameter and a refractive index of $n_D = 1.48 - 1.51$ depending upon the precise composition.

For monochromatic measurements, a 0.5 mW He-Ne laser (lambda = 632.8 nm) acts as light source 2 which is coupled directly into the interferometer component 1 via an objective 3 (f=5 cm) without light conductor 4. An 8 $\mu$m single-mode light-conducting fiber 5 is aligned to the output of the interferometer 1 by means of known precision adjusting means for light-conducting fibers. The light-conducting fiber 5 conducts the interfered light to the detector 6 in the form of a photodiode.

Vapor is metered to the sensor for example via a tube mounted tightly over the measuring arm 11. Air is supplied by a pump to the tube with the evaporated liquid entrained in the air. Such an arrangement was used for the measurement examples shown. A time delay of approximately 20 seconds is present from the switch-on of the metering through the liquid up to the start of the indication of the sensor. This is caused by the necessary displacement of the air in the feed path with the time delay corresponding also to the switchover to a metering of fresh air.

The photopolymerizable polysiloxane VP 1529 of Wacker Chemie is used as a polymer for the superstrate 111 on the measuring arm 11 of the interferometer for the measuring examples shown in FIGS. 2 and 3. After curing, the photopolymerizable polysiloxane VP 1529 has an index of refraction of $n_D = 1.409$ and therefore satisfies the condition for total reflection at the wave guide boundary layer as other polysiloxanes. The refractive index of the superstrate must be less than that of the wave guide. The liquid initial product is easily handled and can be applied in thin layers with good adhesion on glass. The polysiloxane is resistant to acids, lyes and other organic solvents with the exception of halogenated hydrocarbons.

The permeability to gas is approximately 100 times greater than that of nylon or butyl rubber.

VP 1529 has acryl as a terminal group and vinyl, mercaptopropyl and hydrogen as side groups.

VP 1529 displays an intense swelling with the application of hydrocarbons which varies in its extent very greatly in dependence upon the substance.

The polysiloxane layer can be applied selectively to the measuring arm 11 with the use of known techniques of photolithography.

Polysiloxane can be dripped very simply onto the measuring arm 11 by holding the latter downwardly.

Layer thicknesses below 1 μm are also obtained simply when polysiloxane is spread, for example, on water and the interferometer 1 is dipped with a lifting device driven by a step motor with the thin polymer film then being lifted off.

Table 1 shows several relevant substance characteristics for the n-alkanes used for the measurements of FIGS. 2 and 3 as well as several comparison substances. The substance characteristics are refractive index $n_D$, vapor pressure p (at normal conditions) and relative swelling performance of VP 1529 polysiloxane when subjected to these substances referred to n-heptane.

TABLE 1

| Hydrocarbon | Refractive Index nd at 532 nm | Vapor pressure torr at 22° C. | Swelling Capacity (%) |
|---|---|---|---|
| n-pentane | 1.35748 | 450 | 15 |
| n-hexane | 1.37486 | 160 | 33 |
| n-heptane | 1.38764 | 40 | 100 |
| n-octane | 1.39743 | 12 | 182 |
| isooctane | | | 66 |
| m-xylole | | | 502 |
| VP 1529 polysiloxane | 1.40772 | | |

The difference of the refractive indices from pentane toward octane becomes less to polysiloxane. Accordingly, the modulation of the light signal in the interferometer 1 should become smaller in this sequence.

The vapor pressure which drops with molecular size and the increasing swelling capacity however correspond to a greater inclusion of the larger molecules and therefore corresponds to an intensification of the optical effect.

The examples show the large bandwidth of the swelling capacity for various vapors which can be very different for very similar substances such as n-heptane, n-octane and isooctane.

Overall, a very differentiated picture of the substance-dependent influencing of the effective light velocity in the measuring arm 11 of the interferometer 1 is obtained. This is the basis for an interpretation specific of the substance.

FIGS. 2a to 2d show measurement examples with n-pentane, n-hexane, n-heptane and n-octane taken with a cured VP 1529 polysiloxane layer having a thickness of 1.6 μm and a length of 16.1 mm as superstrate 111 over the measuring arm 11 of the interferometer 1.

Each time after 0.75 minutes, the flow of vapor was switched on and a minute thereafter again switched off.

Figure 2A:
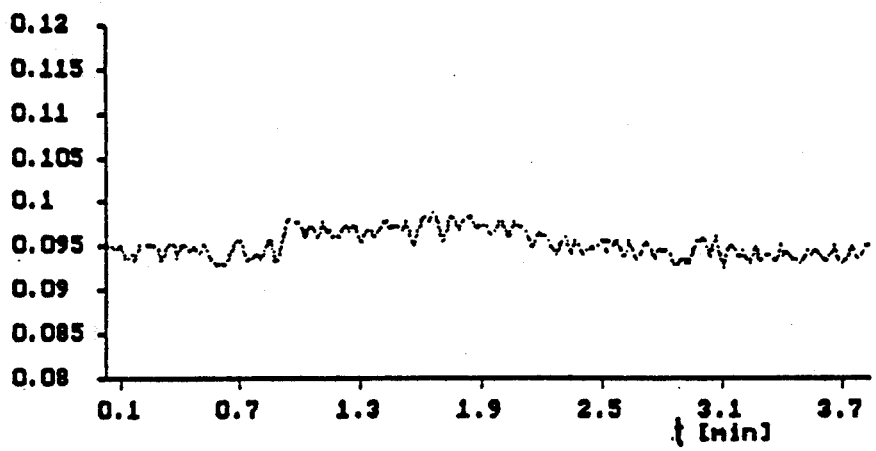
FIG. 2a is a trace of the intensity at the detector as a function of time as a flow of n-pentane is switched on and switched off.
Figure 2B:
FIG. 2b corresponds to FIG. 2a but is for n-hexane.
Figure 2C:
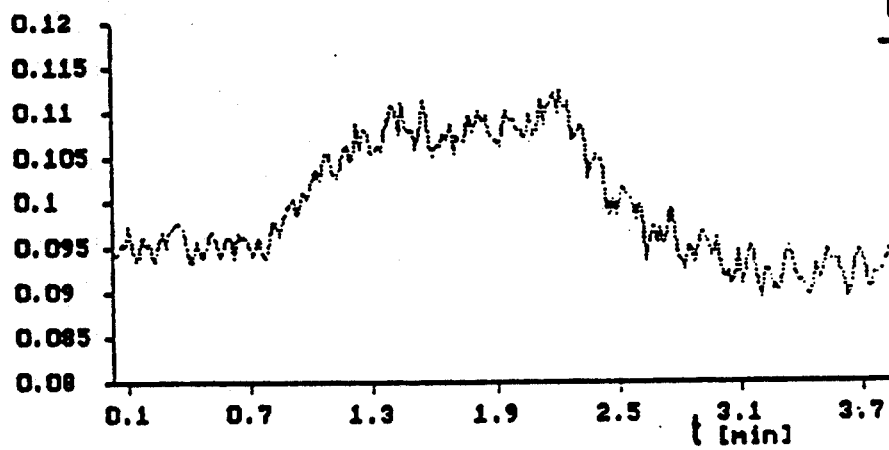
FIG. 2c corresponds to FIG. 2a but is for n-heptane.

The light intensity at detector 6 hardly is distinguishable from noise for n-pentane (FIG. 2a). However, with a flow of vapor, significant interference occurrences are recognizable for n-hexane (FIG. 2b) and n-heptane (FIG. 2c). The slope increase has a varying steepness which can be attributed to the different rapid saturation of the polysiloxane with the alkane or to the different rapid deposits after the flow of vapor has been ended.

Figure 2D:
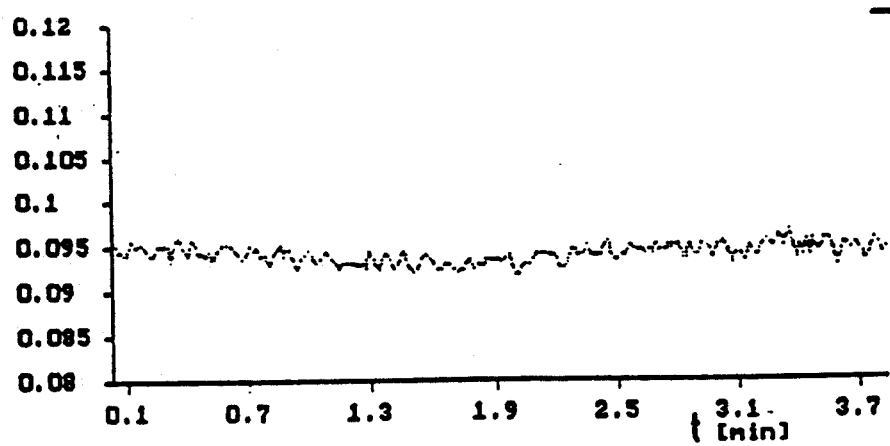
FIG. 2d corresponds to FIG. 2a except that the vapor flow is n-octane.

No significant signal is observed for n-octane (FIG. 2d).

In this way, it can be seen that the described sensor shows different interference effects even for very similar substances which is useful for a tailoring specific to a substance.

FIGS. 3a to 3d show measurement examples for the same substances which have been recorded with a non-cured VP 1529 polysiloxane layer having a thickness of only 400 nm and a length of 13.15 mm. Compared to FIGS. 2a to 2d, a significantly different picture is shown.

Figure 3A:
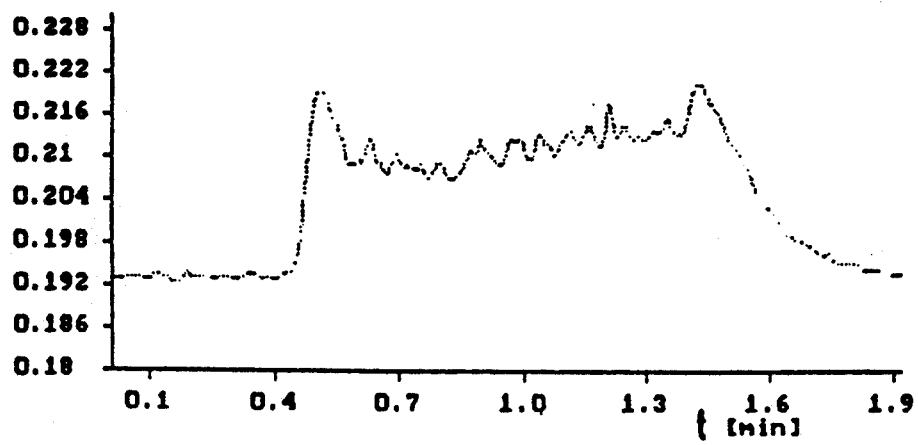
FIG. 3a corresponds to FIG. 2a for n-pentane but with a polymer initial product which is not cured.
Figure 3B:
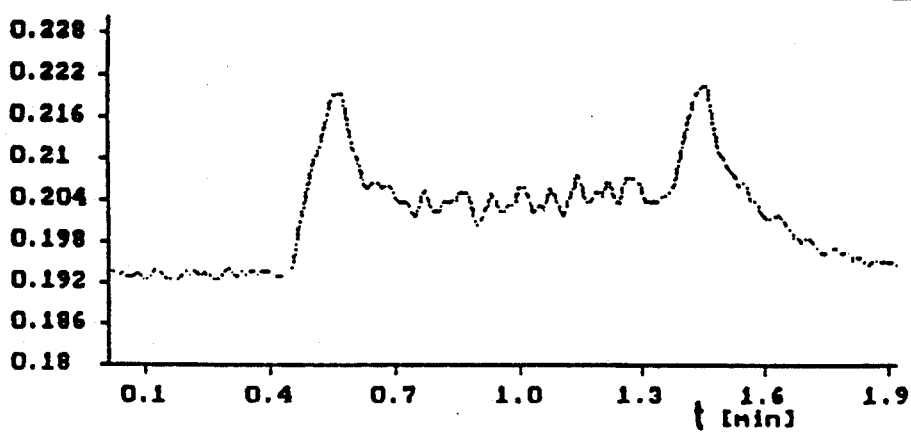
FIG. 3b corresponds to FIG. 3a but is for n-hexane.
Figure 3C:
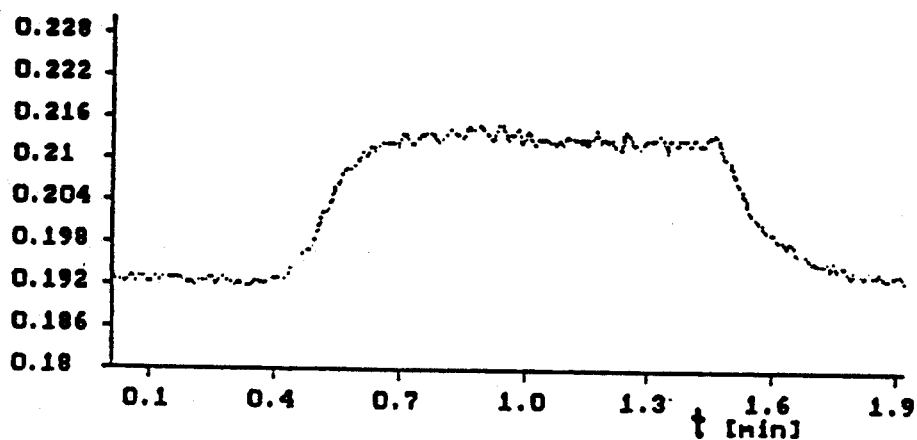
FIG. 3c corresponds to FIG. 3a but is for n-heptane.
Figure 3D:
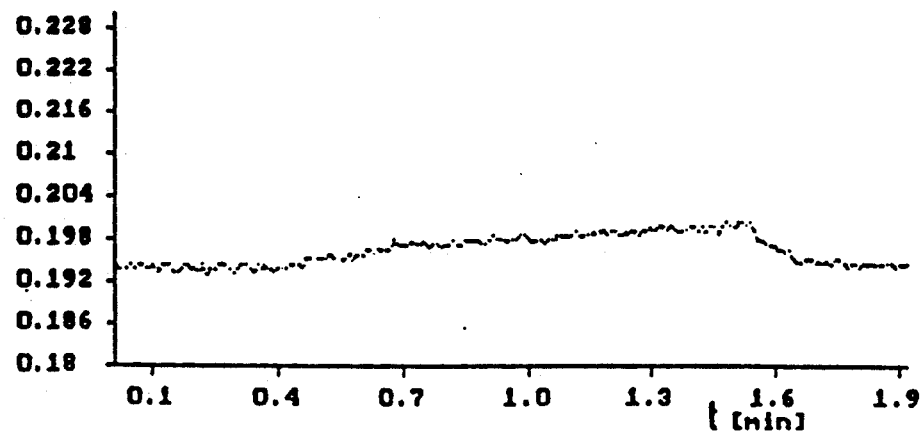
FIG. 3d is the same as FIG. 3a but is for n-octane; and, FIG. 4 is a schematic of an embodiment of the invention including a plurality of interferometers having different polysiloxane polymer superstrates over the measuring arms thereof combined on an integrated optical chip and including a computer evaluation system suited for the application of methods of pattern recognition.

In FIG. 3a, n-pentane now shows an intense signal which shows a maximum at the start and at the end of the flow of vapor. This can be attributed to an interference maximum being exceeded. The influence of n-hexane (FIG. 3b) is also here more intense and therefore the signal between the extremes drops further. N-heptane (FIG. 3c) does not reach the interference maximum. The signal flanks are steeper than in the example shown in FIG. 2c. For n-octane (FIG. 3d), however, a clearly visible signal now occurs even though it is weak.

Without curing, the vapor absorption of the VP 1529 polysiloxane is greater which amplifies the interference effect. However, the length of the superstrate 111 and the thickness thereof are changed with respect to FIGS. 2a to 2d so that the effects of various parameters superpose.

If two Mach-Zehnder interferometers 1 are accommodated on a substrate and if superstrates 111 are applied to the respective measuring arms thereof in accordance with these two examples, then a selection of a specific alkane from the group n-pentane to n-octane, which is supplied to the sensor unknown, can be clearly made from the measuring results in combination.

The identification of substances can be substantially expanded with a larger number of interferometers on a substrate (chip) and with optimal layer variations. This can then be automated with known methods of pattern recognition.

An an embodiment suitable for this is shown in FIG. 4. Here, the embodiment of FIG. 1 is varied in that a plurality, namely, three Mach-Zehnder/Interferometers with comparison arms 12a, 12b, 12c, measuring arms 11a, 11b, 11c and different polysiloxane polymer superstrates 111a, 111b, 111c are arranged on an integrated optical chip 18. The interferometers are connected to three detectors 6a, 6b, 6c having output signals lines 7a, 7b, 7c. Light input is supplied from the light source 2 and the objective 3 (both like in FIG. 1) via alight distributing member 23 and three light-conducting fibers 4a, 4b, 4c. Appropriate light distributing members 23 are readily available. A simple form is realized by distributing a bundle of optical fibers into the three light conducting fibers 4a, 4b, 4c.

The device having three parallel elements (interferometers, et cetera) is just as example, any device from two (as in the example of distinguishing between the three alkanes) to a number as high as considered practical for evaluation may be selected.

The computer 80 is adapted for terminating the three output signal lines 7a, 7b, 7c and for evaluating the inputs by way of a pattern recognition software 81 as known in the art. An output device 82 known in the art, such as a display or a printer is attached. In the measuring examples of FIGS. 3a to 3d, the layer thickness of 400 nm of the superstrate 111 is significantly less than the laser wavelength of 632 nm. With the total reflection at the boundary interface wave guide/superstrate, a substantial portion of the light wave passes through the interface superstrate/(air and vapor). In this way, the position of the boundary layer and the substance composition of the air/vapor-mixture influences the light propagation and the interference in the Mach-Zehnder interferometer 1. It is precisely because of the significant swelling of the polysiloxane specific to the substance that layers which are so thin are advantageous.

A further parameter which can be utilized with the sensor shown for substance identification is the dispersion that is, the wavelength dependency of the refractive index.

Many different measurements can be obtained by changing the laser wavelength with an otherwise unchanged assembly (FIG. 1). These measurements can be compared to known measuring results via pattern recognition methods and can be evaluated to make a substance identification.

All of the measurements can be carried out simultaneously when a polychromatic light source having a continuous spectrum or line spectrum is used and a diode-array spectrometer is used as the detector 6. A light-conducting fiber 4 can be advantageously used for coupling in the light of the light source.

The use of the sensor is not limited to the examples of alkanes shown. Especially hydrocarbon substances, also hydrocarbons containing oxygen and halogens, can be absorbed by polysiloxane and other polymers and can then be interferometrically detected.

It is understood that the foregoing description is that of the preferred embodiments of the invention and that various changes and modifications may be made thereto without departing from the spirit and scope of the invention as defined in the appended claims.

What is claimed is:

1. An optical sensor for detecting a substance, the sensor comprising:
   a wave guide substrate;
   an interferometer optically integrated in said wave guide substrate and having a measuring arm and a comparison arm;
   a polysiloxane polymer applied to said wave guide substrate in the region of said measuring arm; and,
   said polysiloxane polymer being penetrable by said substance and defining a superstrate on said wave guide substrate.

2. The sensor of claim 1, wherein said polysiloxane polymer and said wave guide have respective indices of refraction with the index of refraction of said polysiloxane polymer being less than the index of refraction of said wave guide.

3. The sensor of claim 1, wherein a polychrome light source is used and the spectral dependence of the action of the substance on the measurement arm is evaluated.

4. The sensor of claim 1, wherein the polysiloxane polymer contains, as a functional group, a material selected from the group consisting of vinyl, mercaptopropyl, acryl, phenyl, ethyl and hydrogen.

5. The sensor of claim 1, wherein the substances detected are alkanes.

6. The sensor of claim 1, wherein the substances detected are hydrocarbons including oxygenated hydrocarbons and halogenated hydrocarbons.

7. The sensor of claim 1, wherein said polysiloxane polymer is cured to have a predetermined index of refraction.

8. A sensor for detecting a substance, the sensor comprising:
   a wave guide substrate;
   an interferometer optically integrated in said wave guide substrate and having a measuring arm and a comparison arm;
   a polysiloxane polymer applied to said wave guide substrate in the region of said measuring arm;
   said polysiloxane polymer being penetrated by said substance and defining a superstrate on said wave guide substrate; and,
   said polysiloxane polymer swelling when penetrated by said substance.

9. A sensor for detecting a substance, the sensor comprising:
   a wave guide substrate;
   an interferometer optically integrated in said wave guide substrate and having a measuring arm and a comparison arm;
   a polysiloxane polymer applied to said wave guide substrate in the region of said measuring arm;
   said polysiloxane polymer being penetrate by said substance and defining a superstrate on said wave guide substrate; and,
   said interferometer being a Mach-Zehnder interferometer.

10. A sensor for detecting a substance, the sensor comprising:
    a wave guide substrate;
    an interferometer optically integrated in said wave guide substrate and having a measuring arm and a comparison arm;
    a polysiloxane polymer applied to said wave guide substrate in the region of said measuring arm;
    said polysiloxane polymer being penetrate by said substances and defining a superstrate on said wave guide substrate;
    a tunable light source for illuminating said interferometer; and,
    means for evaluating the spectral dependence of the action of the substance on the measurement arm.

11. An optical sensor for detecting a substance, the sensor comprising:
    a wave guide substrate;
    an interferometer optically integrated in said wave guide substrate and having a measuring arm and a comparison arm;
    a polysiloxane polymer applied to said wave guide substrate in the region of said measuring arm;

said polysiloxane polymer being penetrable by said substance and defining a superstrate on said wave guide substrate; and, a plurality of interferometers having different polymer superstrates over the measuring arms thereof the combined on an integrated optical chip.

12. A sensor for detecting a substance, the sensor comprising:

a wave guide substrate;

a plurality of interferometers optically integrated in said wave guide substrate and having a measuring arm and a comparison arm;

a polysiloxane polymer applied to said wave guide substrate in the region of said measuring arm;

said polysiloxane polymer being penetrable by said substance and defining a superstrate on said wave guide substrate;

said plurality of interferometers having different polymer substrates over the measuring arms thereof and being combined on an integrated optical chip; and, the substance producing different effects in said plurality of interferometers and pattern recognition methods being utilized to identify the substance.

13. A sensor for detecting a substance, the sensor comprising:

a wave guide substrate;

an interferometer optically integrated in said wave guide substrate and having a measuring arm and a comparison arm;

a polysiloxane polymer applied to said wave guide substrate in the region of said measuring arm;

said polysiloxane polymer being penetrable by said substance and defining a superstrate on said wave guide substrate; and, the sensitivity to the substance being adjusted by varying the polymerization of the polymer superstrate.

14. A sensor for detecting a substance, the sensor comprising:

a wave guide substrate;

an interferometer optically integrated in said wave guide substrate and having a measuring arm and a comparison arm;

a polysiloxane polymer applied to said wave guide substrate in the region of said measuring arm;

said polysiloxane polymer being penetrable by said substance and defining a superstrate on said wave guide substrate; and, chromophores or fluorophores being included in said polymer superstrate.

* * * * *

UNITED STATES PATENT AND TRADEMARK OFFICE
CERTIFICATE OF CORRECTION

PATENT NO. : 5,262,842
DATED : November 16, 1993
INVENTOR(S) : Gunter Gauglitz, Jan Ingenhoff & Norbert Fabricius It is certified that error appears in the above-indentified patent and that said Letters Patent is hereby corrected as shown below:

In column 4, line 58: delete "a".
In column 4, line 68: delete "alight" and substitute --a light--.
In column 5, line 6: delete "as" and substitute --an--.
In column 5, line 30: between "dispersion" and "that", insert --,--.
In column 6, line 9: delete "ethyl" and substitute --methyl--.
In column 6, line 27: delete "penetrated" and substitute --penetrable--.
In column 6, line 40: delete "penetrate" and substitute --penetrable--.
In column 6, line 54: delete "penetrate" and substitute --penetrable--.
In column 6, line 55: delete "substances" and substitute --substance--.
In column 7, line 6: delete "the" and substitute --are--.

Signed and Sealed this

Tenth Day of May, 1994

Attest:

BRUCE LEHMAN

Attesting Officer   Commissioner of Patents and Trademarks